United States Patent [19]
Angelone, Jr. et al.

[11] Patent Number: 5,863,525
[45] Date of Patent: *Jan. 26, 1999

[54] COSMETIC FORMULATION

[75] Inventors: Philip P. Angelone, Jr., Wilmington; Nancy M. Karassik, Concord; William R. Grace, Reading, all of Mass.

[73] Assignee: The Gillette Company, Boston, Mass.

[*] Notice: The term of this patent shall not extend beyond the expiration date of Pat, No. 5,587,153.

[21] Appl. No.: 772,316

[22] Filed: Dec. 23, 1996

Related U.S. Application Data

[63] Continuation of Ser. No. 204,898, Mar. 2, 1994, Pat. No. 5,587,153, which is a continuation of Ser. No. 592,570, Oct. 4, 1990, abandoned.

[51] Int. Cl.⁶ .............................. A61K 7/34; A61K 7/38
[52] U.S. Cl. ............................. 424/66; 424/68; 514/938
[58] Field of Search ........................ 424/66, 68; 514/938

[56] References Cited

U.S. PATENT DOCUMENTS

| | | | |
|---|---|---|---|
| 3,957,969 | 5/1976 | Fujiyama | 424/64 |
| 4,120,948 | 10/1978 | Shelton | 424/66 |
| 4,122,029 | 10/1978 | Gee | 514/938 |
| 4,265,878 | 5/1981 | Keil | 424/68 |
| 4,268,499 | 5/1981 | Keil | 424/66 |
| 4,278,655 | 7/1981 | Elmi | 424/47 |
| 4,311,695 | 1/1982 | Starck | 424/185 |
| 4,350,605 | 9/1982 | Hughett | 424/68 |
| 4,383,988 | 5/1983 | Teng | 424/68 |
| 4,673,570 | 6/1987 | Soldati | 424/68 |
| 4,708,863 | 11/1987 | Bews | 424/67 |
| 4,725,431 | 2/1988 | Hourihan | 424/68 |
| 4,782,095 | 11/1988 | Gum | 424/59 |
| 4,944,938 | 7/1990 | Potini | 424/68 |
| 4,948,578 | 8/1990 | Burger et al. | 424/68 |
| 4,980,156 | 12/1990 | Raleigh | 424/66 |
| 5,162,378 | 11/1992 | Guthauser | 514/785 |
| 5,216,033 | 6/1993 | Pereira | 524/844 |
| 5,455,026 | 10/1995 | Bahr et al. | 424/65 |
| 5,456,906 | 10/1995 | Powell | 424/66 |

FOREIGN PATENT DOCUMENTS

| | | |
|---|---|---|
| 291334 | 11/1988 | European Pat. Off. . |
| 0 373 499 | 6/1990 | European Pat. Off. . |
| 2618351 | 1/1989 | France . |
| 2 079 300 | 1/1982 | United Kingdom . |

OTHER PUBLICATIONS

"Arrid Extra Dry Glide–On Product Label", 1985.
"New Silicone Technology for the Preparation of Transparent Cosmetics & Toiletries", Dow Corning Corporation Fifth Scientific Seminar for Personal Care, Sep. 16 & 23, 1987.
"Deodorant & Antiperspirant Formulary", Cosmetics and Toiletries, vol. 100, pp. 65–75, Dec. 1985.
Dow Corning, "Information About Cosmetic Ingredients", 1982.

*Primary Examiner*—Evelyn Huang
*Attorney, Agent, or Firm*—Fish & Richardson P.C.

[57] ABSTRACT

A clear gel-type cosmetic product has a viscosity of at least about 50,000 cps at 21° C., and includes an emulsion with an oil phase and a water phase that includes an incorporated active ingredient. The refractive indices of the water and oil phases match to at least 0.0004, the refractive index of the product is about 1.4000, and the product clarity is better than thirty NTU.

27 Claims, No Drawings

COSMETIC FORMULATION

This is a continuation of application Ser. No. 08/204,898, filed Mar. 2, 1994, U.S. Pat. No. 558,153 which is a continuation of application Ser. No. 07/592,570, filed Oct. 4, 1990, now abandoned.

This invention relates to cosmetic products such as deodorants and antiperspirants and processes for forming such cosmetic products.

Antiperspirant and deodorant products are well-known in the cosmetic art. Deodorant and antiperspirant products may be in the form of an emulsion which includes a water phase and an oil phase. Gel-type emulsion deodorants and antiperspirants are used by rubbing an area of the body such as the underarm to apply a layer of the composition to the skin which reduces odor and/or perspiration. It is desirable that such products have aesthetic characteristics of non-crumbling, smoothness, non-oiliness and non-tackiness. Clarity of such products is a long-sought desirable aesthetic characteristic. Another desirable characteristic is that no readily visible residue as, e.g., a white layer, be left on the skin after the deodorant or antiperspirant is applied.

In accordance with one aspect of the invention, there is provided an optically clear cosmetic product with the ability of being packaged in a clear container, of the deodorant or antiperspirant type that has a refractive index of 1.3975–1.4025 at 21° C., an optical clarity better than fifty NTU (Nephelometric Turbidity Units) at 21° C. and a viscosity of at least about 50,000 cps at 21° C., and is an emulsion with an oil phase and a water phase with an active ingredient incorporated therein. The refractive indices ($\eta_D$) (measured at 5893Å) of the water and oil phases match to within 0.0004. An optically clear antiperspirant or deodorant product of the invention is one that is visually clear, and, like glass, allows ready viewing of objects behind it. By contrast, a translucent deodorant or antiperspirant product, although allowing light to pass through, causes the light to be so scattered that it will be difficult to see clearly objects behind the translucent product. Preferably, the product has a turbidity measurement of less than 30 NTU. Distilled water has a turbidity of 0 NTU and whole milk diluted one part in 350 parts of distilled water has a turbidity of 200 NTU. The turbidity measurements discussed hereinafter were made with a Orbeco-Hellige #965 Direct-Reading Turbidimeter.

The oil phase preferably makes-up about ten to twenty-five percent of the product and includes an emulsifier which when properly mixed with the water phase components yields a water-in-oil emulsion. The oil phase is typically a blend of liquids and includes, a polyorganosiloxane, for example, dimethicone (e.g. Dow Corning DC-225 fluid, $\eta_D$=1.3995), isopropyl myristate ($\eta_d$=1.4340) isopropyl palmitate, ($\eta_D$=1.4370), or diisopropyl sebacate ($\eta_D$=1.4320), and a silicone emulsifying agent. A particularly suitable emulsifying agent is a polyether substituted silicone of Cyclomethicone [and] Dimethicone Copolyol ($\eta_D$=1.3995) (available as DC-3225C from Dow Corning). The DC-3225C emulsifier is useful for preparing stable water-in-silicone emulsions where silicone makes up a large portion of the oil phase, and is a dispersion of a silicone surfactant (dimethicone copolyol) (ten percent) in cyclomethicone (Dow Corning 344 Fluid) (ninety percent).

The water phase includes one or a combination of various polar species such as water ($\eta_D$=1.3333), propylene glycol ($\eta_D$=1.4320), sorbitol ($\eta_D$=1.4611) and ethanol ($\eta_D$=1.3618). The water phase includes, in solution, a deodorant and/or antiperspirant active ingredient such as Triclosan, Benzethonium Chloride and/or an astringent salt of aluminum or zirconium, such as aluminum chlorohydrate or aluminum zirconium tetrachlorohydrex-gly. Particularly preferred active ingredients are a fifty percent aqueous solution of aluminum chlorohydrate ($\eta_D$ of about 1.4070), Triclosan (Irgasan, DP-300, Ciba-Geigy—a 3% solution in ethanol has $\eta_D$=1.3638) and Benzethonium Chloride (Hyamine 1622 Rohn and Haas, a 2% solution in ethanol has $\eta_D$=1.3638). The active ingredient(s) should be present in an amount effective to reduce perspiration or odor, as the case may be, when applied to the skin. The precise amount of active component that can be used will vary with the particular component and formula. As a general rule, however, an antiperspirant product should contain anywhere from about ten to about thirty percent (more preferably about twenty percent to about thirty percent) of active antiperspirant component. A deodorant product should contain up to about 0.5 percent Triclosan, up to about 0.5 percent Benzethonium Chloride or up to about six percent aluminum chlorohydrate as the active deodorant component.

The product can also contain additional cosmetic ingredients such as emollients, colorants, fragrances, and preservatives. Percentages set out in the description and claims are in weight percent.

In preferred embodiments, the oil phase comprises about ten to about twenty-five percent by weight of the product, and the water phase generally makes up between about seventy-five to about ninety percent. To provide an optically clear antiperspirant or deodorant product, the refractive indices ($\eta_D$) of the oil and water phases are measured using a suitable refractometer such as a Reichert-Jung, Abbe Mark II Refractometer Model 10480, and one phase is adjusted as necessary to have a refractive index that matches that of the other phase within 0.0004.

In particular antiperspirant embodiments, the oil phase is formulated and its refractive index is optically measured; the water phase is formulated using a 50% aqueous aluminum chlorohydrate solution, propylene glycol, water and ethanol, and the refractive index of the water phase is optically measured. In a particular deodorant embodiment, the oil phase is formulated and its refractive index is measured. Propylene glycol, water, and ethanol are added to an aluminum chlorohydrate solution and mixed, and sorbitol is then added; and the refractive index of the water phase is then optically measured. In both antiperspirant and deodorant embodiments, propylene glycol or water is added to change the water phase refractive index so that it matches the refractive index ($\eta_D$) of the oil phase to at least 0.0004 at room temperature (20°–25° C.). Following the adjustment, the water phase is optically remeasured to verify the match. For example, for an oil phase with refractive index of 1.3997 and an initial water phase refractive index of 1.3985, propylene glycol is added to the water phase to produce a matching water phase refractive index of 1.3997. The water phase is then slowly added to the oil phase as the mixture is mixed at low speed; fragrance is then added; and the mixture is sheared to form a stable water in oil emulsion with viscosity in excess of 50,000 cps at 21° C. More preferably, the viscosity is between about 80,000–200,000 cps and most preferably around 140,000 cps. The following Examples 1–7 illustrate representative antiperspirant and deodorant products and are given by way of illustration only and are not to be considered as being limiting. The amounts in the Examples and the claims are in weight percent.

In the following Examples, the ingredients of the oil phase are combined and its refractive index at room temperature (about 21° C.) is measured. The water phase is then formulated, its refractive index is measured also at room temperature and adjusted as necessary to match that of the oil phase, and optically remeasured to verify the match. The water phase is then slowly added to the oil phase over about twenty minutes to slowly build viscosity while a mixing head is driven to maintain a mild vortex. Perfume is then added and the mixture is then sheared with a suitable homogenizing device to produce a gel with a viscosity of around 140,000 cps at 21° C.

Example 1 (Antiperspirant)

| CFTA NAME | % ACTIVE |
|---|---|
| WATER PHASE | |
| WATER | 37.01 |
| ALUMINUM CHLOROHYDRATE | 30.00 |
| ETHANOL (SD ALCOHOL 40, 200 PROOF) | 10.00 |
| PROPYLENE GLYCOL | 4.99 |
| OIL PHASE | |
| DIMETHICONE (DC-225) | 9.85 |
| CYCLOMETHICONE & DIMETHICONE COPOLYOL (DC-3225C) | 8.00 |
| FRAGRANCE | |
| FRAGRANCE | 0.15 |

The oil phase had a refractive index of 1.3995 at 21.3° C.; the water phase had an initial refractive index of 1.3990 and the water phase refractive index was adjusted by the addition of propylene glycol so that the water phase refractive index matched the 1.3995 oil phase refractive index. The resulting composition of Example 1 had a viscosity of 146,000 cps, a measured turbidity of 22 NTU and a refractive index of 1.3998 at 21° C., and was an effective antiperspirant.

Example 2 (Antiperspirant)

| CFTA NAME | % ACTIVE |
|---|---|
| WATER PHASE | |
| WATER | 37.01 |
| ALUMINUM CHLOROHYDRATE | 30.00 |
| ETHANOL (SD ALCOHOL 40, 200 PROOF) | 10.00 |
| PROPYLENE GLYCOL | 4.99 |
| OIL PHASE | |
| DIMETHICONE | 10.00 |
| CYCLOMETHICONE & DIMETHICONE COPOLYOL | 8.00 |

The oil phase had a refractive index of 1.3998 at 20.7° C.; and the water phase had a refractive index of 1.3996 at 20.8° C. Its refractive index was not adjusted. The resulting composition of Example 2 had a viscosity of 110,000 cps, a measured turbidity of 18 NTU and a refractive index of 1.3996 at 20.8° C., and was an effective antiperspirant.

Example 3 (Antiperspirant)

| CFTA NAME | % ACTIVE |
|---|---|
| WATER PHASE | |
| WATER | 37.14 |
| ALUMINUM ZIRCONIUM TETRACHLOROHYDREXGLY | 20.00 |
| PROPYLENE GLYCOL | 14.86 |
| ETHANOL (SD ALCOHOL 40, 200 PROOF) | 10.00 |
| OIL PHASE | |
| CYCLOMETHICONE & DIMETHICONE COPOLYOL | 8.00 |
| DIMETHICONE | 10.00 |

The oil phase had a refractive index of 1.3992; the water phase had an initial refractive index of 1.4018 and the water phase refractive index was adjusted by the addition of water so that the water phase refractive index matched the 1.3992 oil phase refractive index. The resulting composition of Example 3 had a viscosity of 140,000 cps, a measured turbidity of 43 NTU, and a refractive index of 1.3992, and was an effective antiperspirant.

Example 4 (Antiperspirant)

| CFTA NAME | % ACTIVE |
|---|---|
| WATER PHASE | |
| WATER | 37.010 |
| ALUMINUM CHLOROHYDRATE | 30.000 |
| ETHANOL (SD ALCOHOL 40, 200 PROOF) | 10.000 |
| PROPYLENE GLYCOL | 4.990 |
| OIL PHASE | |
| DIMETHICONE (DC-225) | 9.825 |
| CYCLOMETHICONE & DIMETHICONE COPOLYOL (DC-3225C) | 8.000 |
| FRAGRANCE | |
| FRAGRANCE | 0.175 |

The oil phase had a refractive index of 1.3997 at 21.0° C.; the water phase had an initial refractive index of 1.3985 at 20.9° C. and the water phase refractive index was adjusted by the addition of 0.5 kilogram of propylene glycol to the 49.3 kilogram water phase so that the water phase refractive index matched the 1.3997 oil phase refractive index. The resulting composition of Example 4 had a viscosity of 122,000 cps, a measured turbidity of 22 NTU, and a refractive index of 1.3997 at 20.7° C., and was an effective antiperspirant.

Example 5 (Antiperspirant)

| CFTA NAME | % ACTIVE |
|---|---|
| WATER PHASE | |
| WATER | 37.010 |
| ALUMINUM CHLOROHYDRATE | 30.000 |
| ETHANOL (SD ALCOHOL 40, 200 PROOF) | 10.000 |
| PROPYLENE GLYCOL | 4.990 |
| OIL PHASE | |
| DIMETHICONE (DC-225) | 9.825 |
| CYCLOMETHICONE & DIMETHICONE COPOLYOL (DC-3225C) | 8.000 |
| FRAGRANCE | |
| FRAGRANCE | 0.175 |

The oil phase had a refractive index of 1.3997 at 20.9° C.; the water phase had an initial refractive index of 1.3995 at 21.0° C. The water phase refractive index was adjusted with propylene glycol to produce a remeasured water phase refractive index of 1.3997 at 20.9° C. The resulting composition of Example 5 had a viscosity of 134,000 cps, a measured turbidity of 18 NTU, and a refractive index of 1.3997 at 20.9° C., and was an effective antiperspirant.

Example 6 (Deodorant)

| CFTA NAME | % ACTIVE |
|---|---|
| WATER PHASE | |
| WATER | 33.25 |
| SORBITOL | 14.00 |
| ETHANOL (SD ALCOHOL 40, 200 PROOF) | 12.00 |
| PROPYLENE GLYCOL | 22.50 |
| TRICLOSAN | 0.25 |
| SODIUM HYDROXIDE | 0.02 |
| OIL PHASE | |
| DIMETHICONE (DC-225) | 9.70 |
| CYCLOMETHICONE & DIMETHICONE COPOLYOL (DC-3225C) | 8.00 |
| FRAGRANCE | |
| FRAGRANCE | 0.30 |

The oil phase had a refractive index of 1.4001 at 19.8° C.; the water phase had an initial refractive index of 1.3998 and its refractive index was adjusted by the addition of propylene glycol to match the 1.4001 oil phase refractive index. The resulting composition of Example 6 had a viscosity of 168,000 cps, a measured turbidity of 26 NTU, and a refractive index of 1.3999 at 24° C., and was an effective deodorant.

Example 7 (Deodorant)

| CFTA NAME | % ACTIVE |
|---|---|
| WATER PHASE | |
| WATER | 35.00 |
| SORBITOL | 14.00 |
| ALUMINUM CHLOROHYDRATE | 3.00 |
| ETHANOL (SD ALCOHOL 40, 200 PROOF) | 10.00 |
| PROPYLENE GLYCOL | 20.00 |
| OIL PHASE | |
| DIMETHICONE (DC-225) | 9.70 |
| CYCLOMETHICONE & DIMETHICONE COPOLYOL (DC-3225C) | 8.00 |
| FRAGRANCE | |
| FRAGRANCE | 0.30 |

The oil phase had a refractive index of 1.3998 at 20.3° C.; the water phase had an initial refractive index of 1.3991 and the water phase refractive index was adjusted by the addition of 0.15 kilogram of propylene glycol to the 49.4 kilogram water phase so that the water phase refractive index matched the 1.3998 oil phase refractive index. The resulting deodorant composition of Example 7 had a viscosity of 160,000 cps, a measured turbidity of 23 NTU, and a refractive index of 1.3997 at 24° C., and was an effective deodorant.

While particular embodiments of the invention has been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. All optically clear antiperspirant or deodorant gel product comprising a water-in-oil emulsion with a viscosity of at least 50,000 cps at 21° C. and a clarity better than 50 NTU at 21° C., said emulsion having
    (a) 75% to 90% of a water phase having dissolved therein a deodorant or antiperspirant active which is one or more astringent salts of aluminum and/or zirconium in an amount effective to reduce odor or perspiration, and
    (b) 10% to 25% of an oil phase comprising a silicone and a silicone emulsifying agent, wherein the silicone emulifying agent is cyclomethicone and dimethicone copolyol.

2. The product of claim 1 wherein the silicone is dimethicone.

3. The product of claim 1 having a viscosity of between 80,000 cps and 200,000 cps at 21° C.

4. The product of claim 1 having a viscosity of between 80,000 cps and 2000,000 cps at 21° C.

5. The product of claim 1 wherein the active is aluminum chlorohydrate.

6. The product of claim 1 wherein the active is an astringent salt of aluminum and zirconium .

7. The product of claim 6 wherein the active is aluminum-zirconium tetrachlorohydrex-gly.

8. The product of claim 1, 5, 6 or 7 which comprises 10% to 30% by weight of the active.

9. The product of claim 1 wherein the water phase further comprises propylene glycol and ethanol.

10. The product of claim 1 wherein the refractive index of the water phase matches the refractive index of the oil phase to at least 0.0004.

11. The product of claim 1 having a refractive index ($\eta_D$) in the range of 1.3975 to 1.4025 at 21° C.

12. The product of claim 3 wherein the active is aluminum chlorohydrate.

13. The product of claim 3 wherein the active is an astringent salt of aluminum and zirconium.

14. The product of claim 13 wherein the active is aluminum-zirconium tetrachlorohydrex-gly.

15. The product of claim 12, 13 or 14 which comprises 10% to 30% by weight of the active.

16. The product of claim 15 wherein the silicone is dimethicone.

17. The product of claim 16 wherein the water phase further comprises propylene glycol and ethanol.

18. A method of producing an optically clear deodorant or antiperspirant gel product having a clarity of better than 50 NTU at 21° C., comprising;
    providing an oil phase comprising a silicone and a silicone emulsifying agent, wherein said silicone emulsifying agent is cyclomethicone and dimethicone copolyol;
    optically determining the refractive index of said oil phase;
    providing a water phase having dissolved therein, in an amount effective to reduce odor or perspiration, a deodorant or antiperspirant active which is one or more astringent salts of aluminum and/or zirconium;
    optically determining the refractive index of said water phase;
    adjusting the refractive index of at least one of said oil and water phases, if necessary, to match that of the other phase to at least 0.0004 at room temperature;
    mixing said oil and water phases; and
    further processing said mixture of said oil and water phases to produce a water-in-oil emulsion having a viscosity of at least 50,000 cps at 21° C.

19. The method of claim 18 wherein said further processing includes shearing the mixture with a homogenizer.

20. The method of claim 19 wherein said further processing produces an emulsion with a viscosity of 80,000 to 200,000 cps at 21° C.

21. The method of claim 18 or 20 wherein the silicone is dimethicone.

22. The method of claim 18 wherein the active is aluminum chlorohydrate.

23. The method of claim 18 wherein the active is an astringent salt of aluminum and zirconium.

24. The method of claim 23 wherein the active is aluminum-zirconium-tetrachlorohydrex-gly.

25. The method of claims 18, 22, 23 or 24 wherein the amount of active is 10% to 30% by weight of the product.

26. The method of claim 25 wherein the water phase further comprises propylene glycol and ethanol.

27. The product of claim 1, 2, 3, 9 or 13 packaged in a container with an optically clear wall.

* * * * *

UNITED STATES PATENT AND TRADEMARK OFFICE
CERTIFICATE OF CORRECTION

PATENT NO. : 5,863,525
DATED : January 26, 1999
INVENTOR(S) : Philip P. Angelone, Jr., et al.

It is certified that error appears in the above-identified patent and that said Letters Patent is hereby corrected as shown below:

ON THE TITLE PAGE:
    Item [56], under OTHER PUBLICATIONS, ""Arrid Extra Dry Glide-On Product Label", 1985", should be --"Arrid Extra Dry Glide-On Product Label", 1985, 1988--.

In col. 6, line 2, claim 1, "All" should be --An--.

In col. 6, lines 18-19, claim 4, delete "4. The product of claim 1 having a viscosity of between 80,000 cps and 200,000 cps at 21°C." and insert --4. The product of claim 1 having a clarity better than 30 NTU at 21°C.--

Signed and Sealed this

Tenth Day of August, 1999

*Attest:*

Q. TODD DICKINSON

*Attesting Officer*      *Acting Commissioner of Patents and Trademarks*